US012685700B2

(12) United States Patent
Jia et al.

(10) Patent No.: US 12,685,700 B2
(45) Date of Patent: Jul. 21, 2026

(54) NATURAL EDIBLE SHAMPOO AND PREPARATION METHOD THEREFOR

(71) Applicant: Ningbo Yufangtang Biological Science and Technology Co., Ltd., Ningbo (CN)

(72) Inventors: Fuhuai Jia, Ningbo (CN); Yunlong Ma, Ningbo (CN); Yuqiang Zheng, Ningbo (CN); Hongjian Tu, Ningbo (CN); Caixia Wang, Ningbo (CN); Feifei Xiong, Ningbo (CN); Pengze Wang, Ningbo (CN); Jie Li, Ningbo (CN); Lihong Chen, Ningbo (CN)

(73) Assignee: Ningbo Yufangtang Biological Science and Technology Co., Ltd., Ningbo (CN)

( * ) Notice: Subject to any disclaimer, the term of this patent is extended or adjusted under 35 U.S.C. 154(b) by 1057 days.

(21) Appl. No.: 17/758,232

(22) PCT Filed: Nov. 13, 2020

(86) PCT No.: PCT/CN2020/128681
§ 371 (c)(1),
(2) Date: Jun. 30, 2022

(87) PCT Pub. No.: WO2021/196628
PCT Pub. Date: Oct. 7, 2021

(65) Prior Publication Data
US 2023/0026434 A1     Jan. 26, 2023

(30) Foreign Application Priority Data
Mar. 31, 2020     (CN) .......................... 202010243399.1

(51) Int. Cl.
| | |
|---|---|
| A61K 8/9789 | (2017.01) |
| A61K 8/365 | (2006.01) |
| A61K 8/37 | (2006.01) |
| A61K 8/44 | (2006.01) |
| A61K 8/55 | (2006.01) |
| A61K 8/60 | (2006.01) |
| A61K 8/64 | (2006.01) |
| A61K 8/73 | (2006.01) |
| A61Q 5/02 | (2006.01) |

(52) U.S. Cl.
CPC .............. *A61K 8/553* (2013.01); *A61K 8/365* (2013.01); *A61K 8/375* (2013.01); *A61K 8/44* (2013.01); *A61K 8/602* (2013.01); *A61K 8/64* (2013.01); *A61K 8/73* (2013.01); *A61K 8/9789* (2017.08); *A61Q 5/02* (2013.01)

(58) Field of Classification Search
CPC ........ A61K 8/553; A61K 8/365; A61K 8/375; A61K 8/44; A61K 8/602; A61K 8/64; A61K 8/73; A61K 8/9789; A61K 8/345; A61K 8/645; A61K 8/88; A61K 8/37; A61K 8/39; A61K 8/63; A61K 8/86; A61K 2800/592; A61Q 5/02; A61Q 5/006; A61Q 5/12
See application file for complete search history.

(56) References Cited

U.S. PATENT DOCUMENTS

| | | | |
|---|---|---|---|
| 2016/0120803 A1* | 5/2016 | Mathur | ................ A61K 8/4993 514/169 |
| 2020/0000692 A1* | 1/2020 | Baldaro | ................... A61K 8/73 |

FOREIGN PATENT DOCUMENTS

| | | | | |
|---|---|---|---|---|
| JP | 2015208241 A | * | 11/2015 | |
| WO | WO-2010026009 A1 | * | 3/2010 | ............. A61K 8/463 |

OTHER PUBLICATIONS

English Translation of JP2015208241A (Year: 2015).*
Scientic Committee on Consumer Safety (SCCS) . (Dec. 2014). Request for an addendum to scientific opinion: Ethyl Lauroyl Arginate HCI (ELA) (P95) . Europa. https://ec.europa.eu/health/scientific_committees/consumer_safety/docs/sccs_0107.pdf (Year: 2014).*
Google English Translation WO2010026009A1 (Year: 2026).*

* cited by examiner

*Primary Examiner* — Bethany P Barham
*Assistant Examiner* — Alexandra Nicole Isnor
(74) *Attorney, Agent, or Firm* — Wang Law Firm, Inc.

(57) ABSTRACT
A natural edible shampoo and preparation method thereof, the components comprises fatty acyl lactyl-lactic acid, arginine, vegetable oleic acid monoglyceride, plant phospholipid, ε-polylysine, ethyl lauroyl arginate hydrochloride, inulin, polyol and so on. It resist static electricity, improve the smoothness of hair, prevent pore clogging, and has good flowability at a low temperature. The shampoo overturns the classic concept of existing cationic hair care (large irritation), uses nearly non-irritant natural anionic wash and care main ingredients, relies on a non-enclosed protein peptide/low HLB value oiliness agent film-forming smoothing system, avoids a cationic polymer/silicone oil hair-care pattern with intensive negative effect, and protects the original ecological environment of hair and scalp, so that a final product gains the smooth experience feeling of organic silicone oil, thereby creating a new path for research and development of food and cosmetic-type wash and care two-in-one shampoos.

17 Claims, No Drawings

NATURAL EDIBLE SHAMPOO AND PREPARATION METHOD THEREFOR

TECHNICAL FIELD OF THE INVENTION

The present invention relates to a natural edible shampoo and a preparation method therefor.

BACKGROUND OF THE INVENTION

Shampoos are one of the products with the largest market scale, the most difficult technological and market competition, and the widest development prospect in the cosmetics industry and even the industry of daily chemical products. The superiority and inferiority of ingredients of shampoos directly affect human health. With the progress of society and the enhancement of the health consciousness of the entire population, people are worry more intensively about many hidden dangers caused by smearing shampoos composed of synthetic chemical components on scalps closest to the brain for a long time. Rational consumers have no longer blindly pursued products produced by brand-name enterprises and followed fashion styles, but advocate safe, environmental-friendly and healthy natural high-tech shampoo products with cosmetics and food homology and wash and care functions. It is expected that the safe and sanitary daily necessities come onto the market.

The concept of the "natural edible products" of the present invention is defined as follows.

(1) Raw materials selected for the product all are food grade raw materials, which may be adapted to manufacture food.

(2) Raw materials selected for the product are natural products in the natural world, or raw materials selected by the product are obtained in such a manner that natural products in the natural world, as raw materials, are scientifically combined (combined by virtue of chemical bonds) without introducing unnaturally formed (i.e., artificially synthesized rather than naturally existent) groups. The core groups of the product all are natural and may be decomposed in the natural world or decomposed, by bio-enzymes of human bodies and other biological decomposition systems, into naturally existent structural products identical to the natural products. Decomposed intermediates of the product are green and environmental-friendly products harmless to human health.

(3) Raw materials selected for the product meet standard requirements of cosmetics without irritant allergies.

It is a superordinate goal pursued in the industry all the time to prepare shampoos with both wash and care functions by virtue of a solution of cosmetics and food homology combined with a natural process. Various famous-brand companies have made unremitting efforts to promote the green and environmental-friendly progress of shampoos.

At the end of the 70s, a first shampoo-BEE&FLOWER shampoo had been born in China. In the 80s, shampoos using simple Chinese medicinal herb formulae came into vogue, with traditional function, such as hair blackening shampoos, anti-hair loss shampoos and itching-relieving shampoos. Before 1988, there had been main domestic shampoo brands such as SEAGULL, BEE&FLOWER and MAXAM in the shampoo market of China, featuring low cost and separated hair-wash and hair-care products. Besides the cleaning ability, they did not have other remarkable functional differences.

In 1986, Unilever entered the Chinese market to produce Lux shampoos. Soon afterwards, Procter&Gamble Company had keenly caught the cognitive gap of Chinese consumers in 1988 and rapidly launched the first anti-dandruff shampoo "Head&Shoulders" in China. "Head&Shoulders" enabled the Chinese consumers to fundamentally change the cognition of dandruff problem. Procter&Gamble Company subsequently released a REJOICE "two-in-one" shampoo in sequence to facilitate the concept of two-in-one, thereby laying the foundation for mainstream research on shampoo products in the future in China. In addition to the Pantene nutritional shampoo later, Procter&Gamble Company occupied the leading position in the market by applying advanced technologies and marketing tools. The market share of the only three brands in the nationwide hair-wash and hair-care market reached up to 60%. Transnational corporations such as Unilever and Kao were attracted to launch shampoo brands such as Lux, Hazeline, Feather, Sifone and Lanbeisi to share the market jointly following the success of Procter&Gamble Company, thereby driving the market to develop rapidly toward high quality, multiple variety and functionality.

In face of the monopoly position of Procter&Gamble Company, Oni and Slek threw down powerful challenges twice. Positioned with plant concept, the outlook of Chinese shampoo market was changed to a great extent. With the opening of market gap, some enterprises also applied unique technologies or brand extension strategies to grab market share in succession. In the meantime, besides brands VS Sassoon and Ascend, Procter&Gamble Company further competed to launch diversified product variety packages, and thus, the market competition in Chinese shampoo market were unprecedentedly intense.

Procter&Gamble Company, by virtue of high-tech multi-brand strategy and localization strategy, achieved continuous product innovation and brand building, with five sub-brands: Head&Shoulders-anti-dandruff, Rejoice-submissive, Pantene-nutritional, VS Sassoon-moist and Clairol-natural, which shares the first group with brands such as Lux, Hazeline, Clear of Unilever, with market share over 70%. Shampoos of brands such as L'Oreal, Slek of C-bons group, Bawang, Guandong Mingchen (Difaso, Mei-wang, Eihsia, Gaoxin kangxiao) and La Fang form the second group. Other domestic brands such as Triatop, Haodi, Oni and La Fang form the third group. Shampoo brands will keep on developing and intrudes into market segments of each other, which promotes decline of market price and forms the pattern of monopolistic competition.

To update the traditional shampoo only with the cleaning effect, the Rejoice "two-in-one" shampoo advocated by Procter&Gamble Company may help soothe hair cuticles and reduce frictional damage by adding silicone oil, namely a polydimethylsiloxane substance in a component table of the shampoo (nearly 90% of shampoos in the market contain silicone oil), so that hair is smooth. Moreover, silicone oil is adsorbed to the surface layers of hair to play a protecting role. However silicon oil is in water and clog hair follicles, resulting in dandruff, itchy scalp and greasy hair, which lead to hair damage and even hair loss.

Silicone oil-free shampoos born at the right moment with a function of preventing pore clogging are becoming a new favorite of daily used chemical enterprises, attracting famous daily used chemical giant companies to follow. It is declared that silicone oil-free shampoo products with better effects on cleaning hair roots have become objects purchased by major daily used chemical brands. Unilever also joined the group of competition in silicone oil-free shampoo and launched Clear silicone oil-free high-end anti-dandruff serial products. Sub-brands Ciairol 0-feel natural series and Pantene pure and bright repair silicone oil-free shampoos of Procter&Gamble Company were marketed in succession. Sub-brands Syoss of German Kenkel, L'Oreal Paris and Uniasia technology Hongkong all launched their silicone oil-free hair-wash and hair-care products, which enabled additives with core functions of shampoos to take a large step towards green, environmental-friendly and safe orientation.

In addition, surfactants of main ingredients of shampoos also underwent a leap from chemically synthesized fatty alcohol sulfates and fatty alcohol-polyoxyethylene ether sulfates (AES) to green, environmental-friendly and safe alkyl glucosides (APG), fatty acyl amino acid salts (amino acid surfactants), fatty acyl taurine slats and fatty acid polyglycerol esters. For example, Seeyoung silicone oil-free amino acid shampoo series of Uniasia Guangzhou had been accepted by the market.

So far, related products in accordance with positioning of concept of the above-mentioned natural edible shampoo were not popular, and technical circle came to a conclusion that formulae and preparation processes had many constraining bottlenecks which were reflected in a centralized manner as follows.

(1) Natural edible combing friction reducing agents capable of replacing organic silicone oil with an excellent smooth effect on hair had not been found yet, so that the combing smoothness of any one green and healthy shampoo could not reach or surpass that of classic silicone oil shampoos at present.

(2) The core auxiliary that supports anti-static property and dry combing friction reducing durability of the shampoo was a chemically synthesized polyquaternium polymer or a chemically modified (a chemical cationized reagent grafted) natural gum, and there was still no substantive breakthrough in exploration of natural edible substitutes or synergistic combination systems of the substances.

(3) The HLB value of the surfactants for food processing was low, most surfactants were emulsifying dispersants featuring weak washing ability, poor foaming property and short duration of foam, so that various dirt in dandruff and hair could not be cleaned by way of washing, suspending and resisting reprecipitation.

(4) The natural edible surfactants were extremely easily hydrolyzed to loss efficacy and were difficult to resist microbial corrosion and deterioration. It was difficult to screen natural edible preservatives, so that the product was poor in stability and short in shelf life, and was hardly commercialized.

(5) Most natural edible components were single in function, insufficient in efficacy powerful degree and low in effective speed, and were inferior in anti-dandruff and itching-relieving aspects, so that the shampoo system composed of their compositions could not compete with chemically synthesized shampoos and could not be popular among people.

In addition, there were many varieties, and the "wash and care mechanism" followed by rapidly iterated commercially-available two-in-one wash and care type shampoos was still as follows.

When a stable mixture composed of a surfactant/a cationic polymer/an oiling agent capable of serving as a detergent was diluted with water in large volume, originally solubilized oily substances were separated from a micellar solubilization system, were demulsified and separated out. By virtue of flocculation of the synthesized cationic polymer, the oily substances were adsorbed to surface of hair to achieve a closed smoothness-increasing "hair-care" effect, so as to complete the hair-wash and hair-care process. The "wash and care mechanism" have dominated research and development of products in shampoo industry all the time and also become a significant barrier that blocks breakthroughs of natural edible shampoo related products.

SUMMARY OF THE INVENTION

It is a first object of the present invention to provide a natural edible shampoo which can resist static electricity, improve the smoothness of hair, prevent pore clogging, and has good flowability at a low temperature.

It is a second object of the present invention to provide a preparation method for the natural edible shampoo. The method is safe, environmental-friendly, and easy and convenient to operate. The prepared natural edible shampoo has the advantages such as wet and dry combing smoothness and fluffiness and elegance of washed and blow-dried hair, which are unique to wash and care two-in-one silicone oil shampoos that make mass consumers "addicted". And the prepared natural edible shampoo has the functions of moisturizing and nourishing scalp, removing dandruff and relieving itching, being safe and non-toxic and being harmless to human health.

For achieving the first object, the natural edible shampoo comprises the following components (in parts by weight):

10-14 parts of fatty acyl lactyl-lactic acid,
4.2-6.5 parts of arginine,
3-5 parts of vegetable oleic acid monoglyceride,
0.2-0.5 parts of plant phospholipid,
0.2-0.8 parts of ε-polylysine,
0.2-0.8 parts of ethyl lauroyl arginate hydrochloride,
1-2 parts of inulin,
0.1-0.8 parts of dipotassium glycyrrhizate,
2-3 parts of diglyceryl fatty acid ester,
3-6 parts of tetraglyceryl olivate,
3-6 parts of polyglyceryl fatty acid ester,
3-5 parts of an alcohol soluble plant protein glycerin solution, and
48.8-69.9 parts of polyol,
the above described components are all selected from food grade raw materials for cosmetics, and may be used for manufacturing food; and the components themselves or each group of the components are naturally derived, and may be decomposed into natural products. The natural edible shampoo of the present invention uses a true sulfate-free formulation and is dedicated to maternal, infant and pregnant uses, and has irritant data which is lower than that of current market-available similar products (still not belonging to cosmetics and food homology) which are the most environmental-friendly, safe and healthy and are modulated by amino acid surfactants.

The shampoo overturns the classic concept of existing cationic hair care (high irritation), uses nearly non-irritant natural anionic wash and care main ingredients, relies on a non-enclosed protein peptide/low HLB value oiliness agent film-forming smoothing system, avoids a cationic polymer/silicone oil hair-care pattern with intensive negative effect, and protects the original ecological environment of hair and scalp, so that a final product gains the smooth experience feeling of organic silicone oil, thereby creating a new path for research and development of food and cosmetic-type wash and care two-in-one shampoos.

In the described solution, the fatty acyl lactyl-lactic acid is prepared by an intermediate-temperature esterification process, and the detail preparation method comprises:

(a) mixing food grade latic acid and food grade fatty acid in a molar ratio of (1.2-1.28):1, and adding the mixture into an inert solvent with water, the weight of the inert solvent is 2-5 times of the total weight of the mixture of the food grade latic acid and the food grade fatty acid; adding a food grade phosphoric acid catalyst which accounts for 0.5% of the total material weight into the above mixture, and esterification and dehydration reactions are performed at not lower than 110-116° C., and wherein the described food grade fatty acid is selected from fatty acids having ten to sixteen carbons; and (b) obtaining generated product after the reactions, the generated product is recrystallized and refined, and is subjected to decoloring and deodorization in a food grade solvent, and finally, the product is recrystallized and refined again to obtain the fatty acyl lactyl-lactic acid.

Preferably, the arginine is anhydrous arginine recrystallized in ethanol.

In the prior art, when a two-in-one shampoo taking conventional sulfate surfactants such as fatty alcohol sulfates (K12) and fatty alcohol-polyoxyethylene ether sulfates (AES) as main ingredients is flushed with a lot of water, the concentration thereof is reduced to a small amount, the originally solubilized oily substances (such as organic silicone oil) are demulsified and separated out and adsorbed onto the surface of hair by virtue of flocculation effect of synthesized cationic polymer substances or cation-modified natural gum, so as to achieve the closed smoothness-increasing "hair-care" effect. However, excessive use of silicone oil will make silicone oil deposited on the surface of hair and hair follicles, which affects the metabolism of hair. Accumulated residues of the cationic polymer with high charge density on the surface of hair are forever pain that puzzles the industry. The nutritional hair-wash pattern of the present invention has features of excellent anti-static property and hair-care smoothness of fatty acyl lactyl-lactic acid arginine, prevents many negative effects caused by the powerful cationic polymers and functions to increase the smoothness and perform hair care.

Preferably, the vegetable oleic acid monoglyceride is a product obtained by a mono-esterification reaction between glycerin and food grade fatty acids having 12 to 32 carbons, and the plant phospholipid is selected from soybean phospholipid, peanut phospholipid and sunflower seed phospholipid, and is most preferably the commercially-available soybean phospholipid. The described vegetable oleic acid monoglyceride is most preferably the commercially-available olive oleic acid monoglyceride.

Preferably, the ε-polylysine is a cationic polypeptide, serving as a food preservative and composed of 25-30 lysine residues, has a degree of polymerization greater than that of decapeptide and has a molecular weight of 3600-4300.

Preferably, the inulin is edible chicory root extract, and the dipotassium glycyrrhizate is edible *glycyrrhiza* extract.

Preferably, the diglyceryl fatty acid ester is an esterification product of food grade fatty acids having eight to twelve carbons and food grade diglyceryl mainly containing straight chains and containing a small amount of loop chains, and is most preferably the commercially-available diglyceryl sesquioctanoate.

Preferably, the tetraglyceryl olivate is an esterification product of food grade olivate and food grade tetraglyceryl mainly containing straight chains and containing a small amount of loop chains; the polyglyceryl fatty acid ester is an esterification product of food grade fatty acids having eight to twelve carbons and food grade hexaglycerol to decaglycerol mainly containing straight chains and containing a small amount of loop chains, and is most preferably the commercially-available decaglycerol octoate; and the food grade alcohol soluble plant protein glycerin solution is a glycerin solution of alcohol soluble wheat proteins or maize proteins with a molecular weight of 10000-30000D, the content of protein being greater than 6%, and is most preferably the commercially-available odorless alcohol soluble wheat proteins.

Preferably, the polyol is selected from glycerin, xylitol, sorbitol or a mixture thereof, and is most preferably medical grade or cosmetics grade glycerin.

The components of the natural edible shampoo of the present invention may further comprise a natural perfume material. The natural perfume material is the commercially-available natural essential oil such as essential oil of jasmine, essential oil of roses, essential oil of chamomile or essential oil of *cananga odorata*.

A preparation method for the natural edible shampoo, comprising the following steps:

(1) Preparation of the Premix a neutralization process:

in a stirring condition, arginine is input into polyol accounting for ½ of the total weight of polyol, high purity nitrogen is blown to the bottom for protection, the temperature is raised to 80-85° C., the arginine is dissolved and dehydrated for at least 1 h, and after the material is completely transparent, the water content is smaller than 0.1%, a material A is obtained;

in a stirring condition, fatty acyl lactyl-lactic acid is input into polyol accounting for ¼ of the total weight of polyol, high purity nitrogen is blown to the bottom for protection, the temperature is raised to 80-85° C., the fatty acyl lactyl-lactic acid is dissolved and dehydrated for at least 20 min, and after the material is in a homogeneous state, the water content is smaller than 0.1%, a material B is obtained; and in a stirring condition, the temperature is controlled at 80-85° C., the material A is slowly poured into the material B in batches, the PH value is strictly controlled to be smaller than 7.2, high purity nitrogen is blown to the bottom for protection, a neutralization reaction is performed for at least 1.5 h, and after the system is completely transparent, a material C is obtained.

a micro-emulsification process:

in a stirring condition, the temperature is controlled at 60-75° C., vegetable oleic acid monoglyceride, diglyceryl fatty acid ester, tetraglyceryl olivate and polyglyceryl fatty acid ester are slowly input into the material C in sequence, are fully mixed for at least 0.5 h, dipotassium glycyrrhizate is input, the mixture is continuously stirred for at least 1.5 h, and after the system is completely transparent, a material D is obtained.

(2) Preparation of a Blending Material in a stirring condition, food grade plant phospholipid is input into polyol accounting for 1/12 of the total weight of polyol, high purity nitrogen is blown to the bottom for protection, the temperature is raised to 55-60° C., the food grade plant phospholipid is melted and dispersed for at least 4 h, and after the material is a homogeneous flowable thick liquid, a material E is obtained;

in a stirring condition, food grade ¿-polylysine and ethyl lauroyl arginate hydrochloride are input into polyol accounting for 1/12 of the total weight of polyol, the temperature is raised to 65-70° C., they are dissolved for at least 0.5 h, and after the material is a completely transparent liquid, a material F is obtained;

in a stirring condition, food grade inulin is input into the residual polyol, the temperature is raised to 65-70° C., the food grade inulin is dissolved for at least 0.5 h, and after the material is a completely transparent liquid, a material G is obtained; and the material D is input into a blending pot, the temperature is strictly controlled to 70-75° C., the rotational speed is controlled at 100-150 rpm, the material E is poured into the material D within 30 min, and the mixture is stirred at a constant temperature for 15 min till the material system is completely transparent; then the materials F and G are dropwise added within 30 min, the temperature is continuously controlled at 70-75° C., the rotational speed is controlled at 150-250 rpm, and the mixture is stirred for 15 min till the material system is completely transparent; the material is cooled to 55-60° C., a food grade alcohol soluble plant protein glycerin solution is added into the described material in batches within 30 min, the rotational speed is controlled at 80-100 rpm, the mixture is stirred at least 45 min till the material system is in a completely transparent low-thickness state, then the rotational speed is controlled at 30-40 rpm, the material is stirred for at least 20 min while cooling, till the temperature of the material is below 35° C., and the natural perfume material is added and the mixture is stirred for at least 20 min, till the material is in a transparent high-thickness flowable colloidal state.

(3) Aging the material obtained in step (2) is placed at room temperature to be aged for 20-30 h to obtain the natural edible shampoo.

Compared with the prior art, the present invention has the following advantages:

The present invention has excellent anti-static hair-care effect of the anionic surfactant, i.e. fatty acyl lactyl-lactic acid argininate by using the anti-static property of arginine on hair, creates a precedent that the edible anionic surfactant serves as an anti-static agent. By matching of polylysine/ethyl lauroyl arginate hydrochloride/fatty acid polyglycerol ester/inulin in cooperation with a natural edible oiliness agent system, hair gains significant smoothing and resistance-reducing effects, and safe and nutritional wash and care of hair enters a brand-new pattern.

Although the inulin (chicory root extract) for healthcare food in the present invention belongs to a nonionic fructose polymer, it shows remarkable anti-static property and hair smoothness-increasing property in amine salt of lactyl-lactic acid, thereby easily eliminating static electricity when blow-dried hair is combed.

In the present invention, the alcohol soluble plant protein glycerin dispersant is jointly acted with the cationic ethyl lauroyl arginate hydrochloride and polylysine, is combined with low-HLB-value nonionic natural oily surfactant (which has moderate film forming permeability and is different from a silicone oil film which is neither air-permeable nor water-permeable), and is firmly adsorbed to the surface of hair to form a protective film which has moderate water-permeable property and good air-permeable property, so that the original ecological environment of hair is maintained, and a durable effect is achieved, thereby creating a smooth effect similar to organic silicone oil. Various negative effects caused by silicone oil clogging hair cutiles are avoided, and a passive situation that completely synthesized or chemically modified easily accumulated high molecular polymers such as polyquaternium which have been relied on in the industry for a long time serve as a wet and dry hair smooth combing long-acting enhancer is also avoided.

The alcohol soluble plant protein/plant phospholipid (containing a natural quaternized structure) system in the present invention shows unexceptionable affinity and permeability to hair due to bonding action, so that plasticity of keratins of hair is easily enhanced. Due to super strong water-retaining property (phospholipid becomes colloidal when encountering water and shows the function of a high water-retaining resin) and anti-static synergistic effect, the fluffy effect of hair is improved to a great extent.

Regarding raw materials of existing food and cosmetics detergents, except expensive ginsenosides, gypenosides and soyasaponins which can foam, most surfactants suitable for serving as the detergents (having an HLB value greater than 20) are extremely difficult to foam. In the present invention, a salt formed by neutralizing fatty acyl lactyl-lactic acid and alkaline amino acid-arginine with ideal foam stability in the optimum ratio is used, which has low cost, is easily popularized, foams powerfully during hair-wash operation, has big, many and durable foams, and may effectively suspend hair dirt hidden at the hair roots and the scalp and may effectively reduce a situation that fine dirt returns to the scalp and clogs some pores.

The anhydrous system constructed by using cheap polyol as a carrier in the present invention solves the problem that fatty acyl lactyl-lactate absorbs moisture and is hydrolyzed after being stored for a long time, and the storage period of the product may be prolonged to two years or longer, thereby exploring a new thought for research and development of a long-acting lactyl-lactate surfactant product. Moreover, with regard to the problem that in the anhydrous system constructed by using polyol as the carrier, the product cannot flow and even is hardened at a low temperature when the content of the surfactant is high and the thickness is high, the present invention uses the edible alcohol soluble plant protein as a strong pour point depressant, such that the product can still flow easily and without being solidified at a low temperature (0-5° C.) in winter, thereby facilitating popularized application.

The ethyl lauroyl arginate hydrochloride and polylysine capable of serving as food preservatives in the present invention have a moderate inhibitory effect on various pathogenic microorganisms including fungi that induce scalp inflammation, and are used in cooperation with an anti-allergy soothing agent dipotassium glycyrrhizate, to create non-irritant, itching-relieving and anti-dandruff effects, being safe, sanitary and harmless to health during long-term use, and avoiding drug resistance and dependence and many negative effects (such as damage to microbial balance of scalp and generation of new allergy) on the health of hair which are caused by chemically synthesized strong anti-dandruff agents (such as ZTP and OCT). The food grade ethyl lauroyl arginate hydrochloride constructs a self-corrosion-resistant system together with polylysine and a polyglycerol ester surfactant which have inhibitory actions themselves, thereby avoiding use of a chemical preservative. The fatty acyl lactyl-lactate argininate with high HLB value cooperates with fatty acid polyglycerol ester with an HLB value greater than 20 to form a system which has strong ability to clean accumulated residue dirt of organic silicone oil and synthesized polymers, and in the system, foams penetrate into pores of scalp to take away deep dirt and clean hair roots, so as to bring a fresh and relaxed original ecological environment to scalp. The products of the present invention may expanded a silicone oil scavenger series.

The components of the formulation of the present invention contain many water-retaining groups such as lactyl-lactic acid and polyglycerol, act on related parts, moisturize hair and scalp while washing, and keep oil-water balance to maintain the original micro-ecological environment. The same product may be used for a long time without frequently changing specifications and models. The shampoo of the present invention is easy to flush, and a very small amount of residues on the scalp are edible components, thereby thoroughly eliminating worries of mass consumers who worry about health hazard caused by excessive absorption of residual unhealthy components of chemical shampoos as there are many pores at the scalp closest to the brain.

DETAILED DESCRIPTION OF THE INVENTION

The present invention will be further described below in detail by embodiments.

Embodiment 1

The natural edible shampoo of the embodiment comprises the following components in parts by weight.

120 kg of 99.8% lauroyl lactyl-lactic acid,
58 kg of anhydrous arginine,
45 kg of 99.5% oleic acid monoglyceride,
3.5 kg of anhydrous soybean phospholipid,
5 kg of 99.8% ε-polylysine,
6 kg of 99.8% ethyl lauroyl arginate hydrochloride,
12 kg of anhydrous inulin,
2 kg of 99.5% dipotassium glycyrrhizate,
23 kg of 99.5% diglyceryl sesquioctanoate,
55 kg of 99.5% tetraglyceryl olivate,
50 kg of 99.5% decaglycerol monooctoate,
50 kg of 6% an alcohol soluble plant protein glycerin solution,
568.5 kg of 99.9% glycerin, and
2 kg of essential oil of roses.

The described components are selected from food grade raw materials usable in cosmetics.

99.8% fatty acid lactyl-lactic acid and 99.8% ethyl lauroyl arginate hydrochloride were purchased from Zhengzhou Mingde Biotechnology Co., Ltd.

99.5% diglyceryl sesquioctanoate and 99.5% decaglycerol monooctoate were purchased from Fushan Yinmei Allied Chemical Science and Technology Ltd.

99.5% tetraglyceryl olivate was supplied by Shanghai Yiheng chemical Co., Ltd.

99.8% ε-polylysine was purchased from Zhengzhou BIN-AFO BIOLOGY Limited Liability Company.

6% alcohol soluble plant protein glycerin solution was purchased from Chongqing Haifan Biochemical Technology Co., Ltd.

Anhydrous inulin was chicory root extract from Sethic, France, with a name of "NATULIN NC100 chicory root conditioner".

Other components were commercially-available products.

A preparation method for the natural edible shampoo in the embodiment comprises the following steps:

(1) Preparation of Premix

A neutralization process:

In a stirring condition, the rotational speed was controlled at 100 rpm, 58 kg of anhydrous arginine was input into 285 kg of glycerin, high purity nitrogen was blown to the bottom for protection, the temperature was raised to 80-85° C., the anhydrous arginine was dissolved and dehydrated for 2 h, and after the material was completely transparent, the water content is smaller than 0.1%, a material A was obtained;

in a stirring condition, the rotational speed was controlled at 80 rpm, 120 kg of 99.8% lauroyl lactyl-lactic acid was input into 142 kg of glycerin, high purity nitrogen was blown to the bottom for protection, the temperature is raised to 80-85° C., the lauroyl lactyl-lactic acid was dissolved and dehydrated for at least 30 min, and after the material was in a homogeneous state, the water content is smaller than 0.1%, a material B was obtained;

in a stirring condition, the rotational speed was controlled at 80 rpm, the temperature was controlled at 80-85° C., the material A was slowly poured into the material B in batches, the PH value was strictly controlled to be smaller than 7.2, high purity nitrogen was blown to the bottom for protection, a neutralization reaction was performed for 2 h, and after the system was completely transparent, a material C was obtained.

A micro-emulsification process:

in a stirring condition, the rotational speed was controlled at 100 rpm, the temperature was controlled at 60-75° C., 45 kg of 99.5% oleic acid monoglyceride, 23 kg of 99.5% dipolyglycerin semioctoate, 55 kg of 99.5% tetraglyceryl olivate and 50 kg of 99.5% polyglyceryl monooctoate were slowly input into the material C in sequence, they were fully mixed for at least 1 h, 2 kg of dipotassium glycyrrhizate was input, the mixture was continuously stirred for 2 h, and after the system was completely transparent, a material D was obtained.

(2) Preparation of a Blending Material

In a stirring condition, the rotational speed was controlled at 80 rpm, 3.5 kg of food grade anhydrous soybean phospholipid was input into 47.4 kg of glycerin, high purity nitrogen was blown to the bottom for protection, the temperature was raised to 55-60° C., the food grade anhydrous soybean phospholipid was melted and dispersed for 4.5 h, and after the material was a homogeneous flowable thick liquid, a material E was obtained;

in a stirring condition, the rotational speed was controlled at 80 rpm, 5 kg of food grade 99.8% ε-polylysine and 6 kg of 99.8% ethyl lauroyl arginate hydrochloride were input into 47.4 kg of glycerin, the temperature was raised to 65-70° C., they were dissolved for 1 h, and after the material was a completely transparent liquid, a material F was obtained;

in a stirring condition, the rotational speed was controlled at 80 rpm, 12 kg of food grade anhydrous inulin was input into 47.3 kg of glycerin, the temperature was raised to 65-70° C., they were dissolved for at least 1 h, and after the material was a completely transparent liquid, a material G was obtained; and the material D was input into a blending pot, the temperature was controlled strictly to 70-75° C., the rotational speed was controlled at 100 rpm, the material E was poured into the material D within 30 min, and the mixture was stirred at a constant temperature for 15 min till the material system was completely transparent; then the materials F and G were dropwise added within 30 min, the temperature was continuously controlled at 70-75° C., the rotational speed was controlled at 150 rpm, and the mixture was stirred for 15 min till the material system was completely transparent; the material was cooled to 55-60° C., 50 kg of food grade 6% alcohol soluble plant protein glycerin solution was added into the described material in batches within 30 min, the rotational speed was controlled at 80 rpm, the mixture was stirred at least 1 h till the material system was in a completely transparent low-thickness state, then the rotational speed was controlled at 30 rpm, the material was stirred for at least 20 min while cooling till the temperature of the material was below 35° C., and 2 kg of essential oil of roses was added and the mixture was stirred for at least 30 min, till the material was in a transparent high-thickness flowable colloidal state.

(3) Aging

The material obtained in step (2) was placed at room temperature to be aged for 24 h to obtain the natural edible shampoo. The shampoo was a flowable slightly thick transparent liquid, and the thickness in winter (0-4° C.) did not exceed 3500 mPa·s.

Embodiment 2

The natural edible shampoo of the embodiment comprises the following components in parts by weight.

140 kg of 99.8% cocoyl lactyl-lactic acid,
65 kg of anhydrous arginine,
50 kg of 99.5% olive oleic acid monoglyceride,
4.5 kg of anhydrous soybean phospholipid,
8 kg of 99.8% ε-polylysine,
8 kg of 99.8% ethyl lauroyl arginate hydrochloride,
18 kg of anhydrous inulin,
6 kg of 99.5% dipotassium glycyrrhizate,
30 kg of 99.5% diglyceryl sesquioctanoate,
60 kg of 99.5% tetraglyceryl olivate,
60 kg of 99.5% hexaglycerol monooctoate,
35 kg of 6% an alcohol soluble plant protein glycerin solution,
513 kg of 99.9% glycerin, and
2.5 kg of essential oil of jasmine.

The described components are selected from food grade raw materials usable in cosmetics.

99.8% cocoyl-lactic acid and 99.8% ethyl lauroyl arginate hydrochloride were supplied by Zhengzhou Mingde Biotechnology Co., Ltd.

99.5% diglyceryl sesquioctanoate and 99.5% hexaglycerol monooctoate were supplied by Fushan Yinmei Allied Chemical Science and Technology Ltd.

99.5% olive oleic acid monoglyceride and 99.5% tetraglyceryl olivate were supplied by Shanghai Yiheng chemical Co., Ltd.

99.8% ε-polylysine was supplied by Zhengzhou BINAFO BIOLOGY Limited Liability Company.

6% alcohol soluble plant protein glycerin solution was supplied by Chongqing Haifan Biochemical Technology Co., Ltd.

Anhydrous inulin was chicory root extract of Sethic, France, with a name of "NATULIN NC100 chicory root conditioner".

Other components were commercially-available products.

A preparation method for the natural edible shampoo in the embodiment comprises the following steps:

(1) Preparation of Premix

A neutralization process:

In a stirring condition, the rotational speed was controlled at 150 rpm, 65 kg of anhydrous arginine was input into 256.5 kg of glycerin, high purity nitrogen was blown to the bottom for protection, the temperature was raised to 80-85° C., the anhydrous arginine was dissolved and dehydrated for 2 h, and after the material was completely transparent, the water content is smaller than 0.1%, a material A was obtained;

in a stirring condition, the rotational speed was controlled at 100 rpm, 140 kg of 99.8% cocoyl-lactic acid was input into 128.3 kg of glycerin, high purity nitrogen was blown to the bottom for protection, the temperature is raised to 80-85° C., the lauroyl lactyl-lactic acid was dissolved and dehydrated for at least 30 min, and after the material was in a homogeneous state, the water content is smaller than 0.1%, a material B was obtained;

in a stirring condition, the rotational speed was controlled at 100 rpm, the temperature was controlled at 80-85° C., the material A was slowly poured into the material B in batches, the PH value was strictly controlled to be smaller than 7.2, high purity nitrogen was blown to the bottom for protection, a neutralization reaction was performed for 2 h, and after the system was completely transparent, a material C was obtained.

A micro-emulsification process:

In a stirring condition, the rotational speed was controlled at 150 rpm, the temperature was controlled at 60-75° C., 50 kg of 99.5% olive oleic acid monoglyceride, 30 kg of 99.5% dipolyglycerin semioctoate, 60 kg of 99.5% tetraglyceryl olivate and 60 kg of 99.5% polyglyceryl monooctoate were slowly input into the material C in sequence, they were fully mixed for at least 1 h, 6 kg of 99.5% dipotassium glycyrrhizate was input, the mixture was continuously stirred for 2 h, and after the system was completely transparent, a material D was obtained.

(2) Preparation of a Blending Material

In a stirring condition, the rotational speed was controlled at 100 rpm, 4.5 kg of food grade anhydrous soybean phospholipid was input into 42.75 kg of glycerin, high purity nitrogen was blown to the bottom for protection, the temperature was raised to 55-60° C., the food grade anhydrous soybean phospholipid was melted and dispersed for 4.5 h, and after the material was a homogeneous flowable thick liquid, a material E was obtained;

in a stirring condition, the rotational speed was controlled at 100 rpm, 8 kg of food grade 99.8% ε-polylysine and 8 kg of 99.8% ethyl lauroyl arginate hydrochloride were input into 42.75 kg of glycerin, the temperature was raised to 65-70° C., they were dissolved for 1 h, and after the material was a completely transparent liquid, a material F was obtained;

in a stirring condition, the rotational speed was controlled at 100 rpm, 18 kg of food grade anhydrous inulin was input into 42.75 kg of glycerin, the temperature was raised to 65-70° C., they were dissolved for at least 1 h, and after the material was a completely transparent liquid, a material G was obtained; and the material D was input into a blending pot, the temperature was controlled strictly to 70-75° C., the rotational speed was controlled at 150 rpm, the material E was poured into the material D within 30 min, and the mixture was stirred at a constant temperature for 15 min till the material system was completely transparent; then the materials F and G were dropwise added within 30 min, the temperature was continuously controlled at 70-75° C., the rotational speed was controlled at 250 rpm, and the mixture was stirred for 15 min till the material system was completely transparent; the material was cooled to 55-60° C., 35 kg of food grade 6% alcohol soluble plant protein glycerin solution was added into the described material in three batches within 30 min, the rotational speed was controlled at 100 rpm, the mixture was stirred at least 1 h till the material system was in a completely transparent low-thickness state, then the rotational speed was controlled at 40 rpm, the material was stirred for at least 20 min while cooling till the temperature of the material was below 35° C., and 2.5 kg of essential oil of jasmine was added and the mixture was stirred for at least 30 min till the material was in a transparent high-thickness flowable colloidal state.

(3) Aging

The material obtained in step (2) was placed at room temperature to be aged for 24 h to obtain the natural edible shampoo gel with good transparency, the room temperature thickness being not smaller than 8000 mPa·s, and the natural edible shampoo gel might be packaged in an extrusion paste tube.

Referring to related national standards and industrial standards, related performance indexes of the natural edible shampoo of the present invention and the commercially-available shampoos are compared and detected in detail below.

(I) Basic Performance of the Natural Edible Shampoo of the Present Invention and a Comparison Sample of the Commercially-Available Amino Acid Silicone Oil-Free Shampoo, i.e. Safebola Enjoy Peptide0% Silicone Oil Shampoo on Scalp Care Aspect are Assayed in Detail, Shown in Table 1.

TABLE 1

| Detection items | Detection requirements/detection methods | Detection results | |
| --- | --- | --- | --- |
| | | The natural edible shampoo of the embodiment 1 | The commercially-available amino acid silicone oil-free shampoo: Safebola Enjoy Peptide 0% silicone oil shampoo |
| PH value | Precision test paper | 6.8 | 6.9 |
| Moisture rate of head skin after washing, % | SK-IV digital skin moisture detector (Shenzhen Kakusun) detects the moisture rate of head skin 1 h after hair are washed and blow-dried, and an average value of ten tests of a same testee is taken. | 62 | 45 |

Related data in table 1 shows that the key indexes of the natural edible shampoo of the present invention, such as PH value and moisturizing effect of scalp are excellent than those of the commercially-available amino acid silicone oil-free shampoo.

(II) Toxicological Evaluation

Referring to related steps of acute oral toxicity test in part 2 of toxicological evaluation program of chemicals and test method GBZ/T240.2-2011, the acute oral toxicity LD50 of the described natural edible shampoo to rats is greater than 24800 mg/kg, verifying that the product series of the present invention are in a non-toxic range, thereby indirectly verifying that health is not harmed if the natural edible shampoo of the present invention is eaten by accident as its metabolic intermediate and final products are in the non-toxic range.

(III) Comparison in Irritation Between the Natural Edible Shampoo of the Present Invention and the Commercially-Available Shampoos (Comprising Two-In-One Silicone Oil Shampoos and Amino Acid Silicone Oil-Free Shampoos)

Test Method: Maize Alcohol Soluble Protein Method

Method principle: zein which is nearly completely insoluble in water is acted with the surfactant, so that the water solubility thereof is increased. The surfactant with higher irritation is easier to dissolve zein than the surfactant with lower irritation. Therefore, in accordance with change condition of nitrogen contents after and before action of the surfactant in an aqueous solution, the dissolubility after zein is acted with the surfactant is measured, and the nitrogen content (zein value unit is based on g/L) in dissolved zein is in direct proportion to skin irritation induced by the surfactant, and therefore, the degree of irritation of the surfactant may be known.

Reason for judgment: Zein>4 highly irritant; 2<Zein<4 lowly irritant; Zein<2, non-irritant.

The detection result is as shown in table 2.

TABLE 2

| Product name | Product source | Test results (g/L) | Note |
| --- | --- | --- | --- |
| The natural edible shampoo | Embodiment 1 | 0.012 | The product is diluted by 10 times with water |
| Sulfate two-in-one silicone oil shampoo Safebola Enjoy Peptide dandruff soft shampoo | Commercially-available | 5.28 | |
| The amino acid silicone oil-free shampoo: Safebola Enjoy Peptide 0% silicone oil shampoo | Commercially-available | 1.82 | |

It may be known from data of table 2 that the natural edible shampoo of the present invention is much less irritant to head skin than various commercially-available shampoos.

(IV) Comparison in Hair Bunch High-Temperate-Resistant Blowing Test after Washing Between the Natural Edible Shampoo of the Present Invention and the Commercially-Available Shampoos (Comprising Two-In-One Silicone Oil Shampoos Such as Safebola Enjoy Peptide Dandruff Soft Shampoo and Amino Acid Silicone Oil-Free Shampoos Such as Safebola Enjoy Peptide0% Silicone Oil Shampoo)

Through a high-temperature (60° C.) blowing (5 min each time) test by a blower, hair bunches washed with the commercially-available shampoos (comprising two-in-one silicone oil shampoos and amino acid silicone oil-free shampoos) are somewhat yellowing after being blown for 10 times, and are coarse and withered. Many hairlines may be seen broken after hair bunches are combed.

The hair bunches washed with the natural edible shampoo of the present invention are still kept flexible and bright after being blown (5 min each time) at high temperature (60° C.) for 50 times, verifying that it may protect the hair quality and is afraid of blowing. No broken hair are found in a glass utensil after the hair bunches are combed for 20 times, verifying that the product may nourish hairlines and reduce broken hair effectively.

(V) Comparison in Related Mechanical Data of Combing Improvement Degree after Washing Between the Natural Edible Shampoo of the Present Invention and the Commercially-Available Shampoos (Comprising Two-In-One Silicone Oil Shampoos Such as Safebola Enjoy Peptide Dandruff Soft Shampoo and Amino Acid Silicone Oil-Free Shampoos Such as Safebola Enjoy Peptide0% Silicone Oil Shampoo) Tested by a Tension Tester Method 1. Overview Tension tester is a test instrument dedicated to hair combing performance evaluation, and the action of combing hair by people is simulated by a standard comb to comb a bunch of hair and is recorded by a terminal. When the comb passes through hair fibers, it shows a force (unit: gf) loaded in an appointed displacement (unit: mm) when the comb overcomes hair resistance and stretch. The care effect of shampoo or hair-care product is evaluated by detecting dry and wet combing force decreasing indexes of the hair bunches after and behind the sample is used.

All changed hair qualities (such as chemical treatment, degreasing and hair treatment with polymers) may be tested by the combing resistance, which all will lead to increase of dry hair combing resistance. Effect of components of all types on the hair combing effect is evaluated as the tension tester tests the dry hair combing property.

2. Materials and Methods

2.1 Main Instruments and Materials

Tension tester.
Constant temperature and humidity incubator.
Several hair bunches: 50 cm long, 16 g in weight.
Shampoo: the natural edible shampoo of the present invention and the commercially-available shampoos (comprising two-in-one silicone oil shampoos such as Safebola Enjoy Peptide dandruff soft shampoo and amino acid silicone oil-free shampoos such as Safebola Enjoy Peptide 0% silicone oil shampoo)

2.2 Pre-Treatment of Hair Bunches

Several hair bunches with same length (50 cm) and weight (about 16 g) were prepared. First, the hair bunches were cleaned with 40° C. tap water twice; then they were placed in a beaker containing 5 g of lauryl sodium sulfate and 1000 ml of water, and were heated to 80° C. to be soaked; then the beaker was placed in 45° C. constant temperature and humidity incubator for two hours; and finally, the hair bunches were flushed with tap water till no foam was available and were naturally aired.

Treatment of hair bunch shampoo: 4 g of a tested shampoo sample was weighed, rubbed to the treated hair bunches till foam was uniform, the hair bunches were left still for 5 min, and were flushed with tap water till no foam was available, and the hair bunches were naturally aired.

2.3 Combing Property Test

Dry combing properties of the hair bunches treated by the shampoos were tested respectively on the tension tester.

(1) The tension tester was connected with a power supply of a main frame, a computer was turned on, and the instrument was preheated for over half an hour.

(2) All specimens forming the test sample were collected together, and each specimen was identified. A software was opened to create a new sample, select the test method and name the new sample.

(3) Hair were combed with a plastic comb first, then a to-be-tested hair sample was fixed with a proper fixture, and the hair bunches were naturally placed in the middle of the comb.

(4) After calibrating and zeroing the instrument, it was started to test the hair bunches, the hair bunches were stretched at a rate of 300 mm/min, the displacement was 200 mm, and a load value with the displacement between 100 mm and 200 mm was taken. In order to reduce the measurement errors caused by different hair bunches, the same hair bunch was repeatedly tested for 5 times, and an average value (the program recorded data automatically and calculated the average value) was taken.

3 Results and Discussion

The test mainly examines the combing improvement degree after washing by the natural edible shampoo of the present invention and the commercially-available two-in-one silicone oil shampoos such as Safebola Enjoy Peptide dandruff soft shampoo and amino acid silicone oil-free shampoos such as Safebola Enjoy Peptide0% silicone oil shampoo, and the amplitude of the dry hair combing forces is compared by testing and recording the average load value (gf) of the hair bunches treated by the three shampoos through the tension tester. A data result is below.

| Specimen name | Average load value (gf) |
| --- | --- |
| Natural edible shampoo of embodiment 1 | 22.26835 |
| Commercially-available two-in-one silicone oil shampoo Safebola Enjoy Peptide dandruff soft shampoo | 23.26667 |
| Commercially-available amino acid silicone oil-free shampoo: Safebola Enjoy Peptide 0% silicone oil shampoo | 36.53742 |

It may be seen from the described table that the average load value (gf) for hair dry combing after washing by the natural edible shampoo of the present invention is smaller than those of the commercially-available two-in-one silicone oil shampoos and the amino acid silicone oil-free shampoos, verifying that it may bring nourishing feeling to hair obviously, counteracting astringency caused by balancing degreasing of the surfactant. Its dry combing property is better than that of the commercially-available amino acid silicone oil-free shampoos, reaching an experience effect similar to the commercially-available two-in-one silicone oil shampoos.

The invention claimed is:

1. A natural edible shampoo, comprising the following components (in parts by weight):
   10-14 parts of fatty acyl lactyl-lactic acid,
   4.2-6.5 parts of arginine,
   3-5 parts of vegetable oleic acid monoglyceride,
   0.2-0.5 parts of plant phospholipid,
   0.2-0.8 parts of ε-polylysine,
   0.2-0.8 parts of ethyl lauroyl arginate hydrochloride,
   1-2 parts of inulin,
   0.1-0.8 parts of dipotassium glycyrrhizate,
   2-3 parts of diglyceryl fatty acid ester,
   3-6 parts of tetraglyceryl olivate,
   3-6 parts of polyglyceryl fatty acid ester,
   3-5 parts of an alcohol soluble plant protein glycerin solution, and
   48.8-69.9 parts of polyol,
   the above described components are all selected from food grade raw materials for cosmetics.

2. The shampoo of claim 1, wherein the fatty acyl lactyl-lactic acid is prepared by an intermediate-temperature esterification process, and the detail preparation method comprises:
   (a) mixing food grade latic acid and food grade fatty acid in a molar ratio of (1.2-1.28):1, and adding the mixture into an inert solvent with water, the weight of the inert solvent is 2-5 times of the total weight of the mixture of the food grade latic acid and the food grade fatty acid;

adding a food grade phosphoric acid catalyst which accounts for 0.5% of the total material weight into the above mixture, and esterification and dehydration reactions are performed at not lower than 110-116° C.;

(b) obtaining generated product after the reactions, the generated product is recrystallized and refined, and is subjected to decoloring and deodorization in a food grade solvent, and finally, the product is recrystallized and refined again to obtain the fatty acyl lactyl-lactic acid.

3. The shampoo of claim 1, wherein the arginine is anhydrous arginine recrystallized in ethanol.

4. The shampoo of claim 1, wherein the vegetable oleic acid monoglyceride is a product obtained by a mono-esterification reaction between glycerin and food grade fatty acids having 12 to 32 carbons, and the plant phospholipid is selected from soybean phospholipid, peanut phospholipid and sunflower seed phospholipid.

5. The shampoo of claim 1, wherein the ε-polylysine is a cationic polypeptide, serving as a food preservative and composed of 25-30 lysine residues, has a degree of polymerization greater than that of decapeptide and has a molecular weight of 3600-4300.

6. The shampoo of claim 1, wherein the inulin is edible chicory root extract, and the dipotassium glycyrrhizate is edible *glycyrrhiza* extract.

7. The shampoo of claim 1, wherein the diglyceryl fatty acid ester is an esterification product of food grade fatty acids having eight to twelve carbons and food grade diglyceryl mainly containing straight chains and containing a small amount of loop chains.

8. The shampoo of claim 1, wherein the tetraglyceryl olivate is an esterification product of food grade olivate and food grade tetraglyceryl mainly containing straight chains and containing a small amount of loop chains;

the polyglyceryl fatty acid ester is an esterification product of food grade fatty acids having eight to twelve carbons and food grade hexaglycerol to decaglycerol mainly containing straight chains and containing a small amount of loop chains; and the food grade alcohol soluble plant protein glycerin solution is a glycerin solution of alcohol soluble wheat proteins or maize proteins with a molecular weight of 10000-30000D, the content of protein being greater than 6%.

9. The shampoo of claim 1, wherein the polyol is selected from glycerin, xylitol, sorbitol or a mixture thereof.

10. A preparation method for the natural edible shampoo of claim 1, comprising the following steps:

(1) preparation of premix a neutralization process:

in a stirring condition, arginine is input into polyol accounting for ½ of the total weight of polyol, high purity nitrogen is blown to the bottom for protection, the temperature is raised to 80-85° C., the arginine is dissolved and dehydrated for at least 1 h, and after the material is completely transparent, the water content is smaller than 0.1%, a material A is obtained;

in a stirring condition, fatty acyl lactyl-lactic acid is input into polyol accounting for ¼ of the total weight of polyol, high purity nitrogen is blown to the bottom for protection, the temperature is raised to 80-85° C., the fatty acyl lactyl-lactic acid is dissolved and dehydrated for at least 20 min, and after the material is in a homogeneous state, the water content is smaller than 0.1%, a material B is obtained;

in a stirring condition, the temperature is controlled at 80-85° C., the material A is slowly poured into the material B in batches, the PH value is strictly controlled to be smaller than 7.2, high purity nitrogen is blown to the bottom for protection, a neutralization reaction is performed for at least 1.5 h, and after the system is completely transparent, a material C is obtained;

a micro-emulsification process:

in a stirring condition, the temperature is controlled at 60-75° C., vegetable oleic acid monoglyceride, diglyceryl fatty acid ester, tetraglyceryl olivate and polyglyceryl fatty acid ester are slowly input into the material C in sequence, are fully mixed for at least 0.5 h, dipotassium glycyrrhizate is input, the mixture is continuously stirred for at least 1.5 h, and after the system is completely transparent, a material D is obtained;

(2) preparation of a blending material in a stirring condition, food grade plant phospholipid is input into polyol accounting for ¹⁄₁₂ of the total weight of polyol, high purity nitrogen is blown to the bottom for protection, the temperature is raised to 55-60° C., the food grade plant phospholipid is melted and dispersed for at least 4 h, and after the material is a homogeneous flowable thick liquid, a material E is obtained;

in a stirring condition, food grade ε-polylysine and ethyl lauroyl arginate hydrochloride are input into polyol accounting for ¹⁄₁₂ of the total weight of polyol, the temperature is raised to 65-70° C., they are dissolved for at least 0.5 h, and after the material is a completely transparent liquid, a material F is obtained;

in a stirring condition, food grade inulin is input into the residual polyol, the temperature is raised to 65-70° C., the food grade inulin is dissolved for at least 0.5 h, and after the material is a completely transparent liquid, a material G is obtained;

the material D is input into a blending pot, the temperature is strictly controlled to 70-75° C., the rotational speed is controlled at 100-150 rpm, the material E is poured into the material D within 30 min, and the mixture is stirred at a constant temperature for 15 min till the material system is completely transparent;

then the materials F and G are dropwise added within 30 min, the temperature is continuously controlled at 70-75° C., the rotational speed is controlled at 150-250 rpm, and the mixture is stirred for 15 min till the material system is completely transparent; the material is cooled to 55-60° C., a food grade alcohol soluble plant protein glycerin solution is added into the described material in batches within 30 min, the rotational speed is controlled at 80-100 rpm, the mixture is stirred at least 45 min till the material system is in a completely transparent low-thickness state, then the rotational speed is controlled at 30-40 rpm, the material is stirred for at least 20 min while cooling, till the temperature of the material is below 35° C., and the natural perfume material is added and the mixture is stirred for at least 20 min, till the material is in a transparent high-thickness flowable colloidal state;

(3) aging the material obtained in step (2) is placed at room temperature to be aged for 20-30 h to obtain the natural edible shampoo.

11. The shampoo of claim 2, wherein the arginine is anhydrous arginine recrystallized in ethanol.

12. The shampoo of claim 2, wherein the vegetable oleic acid monoglyceride is a product obtained by a mono-esterification reaction between glycerin and food grade fatty acids having 12 to 32 carbons, and the plant phospholipid is selected from soybean phospholipid, peanut phospholipid and sunflower seed phospholipid.

13. The shampoo of claim 2, wherein the ε-polylysine is a cationic polypeptide, serving as a food preservative and composed of 25-30 lysine residues, has a degree of polymerization greater than that of decapeptide and has a molecular weight of 3600-4300.

14. The shampoo of claim 2, wherein the inulin is edible chicory root extract, and the dipotassium glycyrrhizate is edible *glycyrrhiza* extract.

15. The shampoo of claim 2, wherein the diglyceryl fatty acid ester is an esterification product of food grade fatty acids having eight to twelve carbons and food grade diglyceryl mainly containing straight chains and containing a small amount of loop chains.

16. The shampoo of claim 2, wherein the tetraglyceryl olivate is an esterification product of food grade olivate and food grade tetraglyceryl mainly containing straight chains and containing a small amount of loop chains;

the polyglyceryl fatty acid ester is an esterification product of food grade fatty acids having eight to twelve carbons and food grade hexaglycerol to decaglycerol mainly containing straight chains and containing a small amount of loop chains; and the food grade alcohol soluble plant protein glycerin solution is a glycerin solution of alcohol soluble wheat proteins or maize proteins with a molecular weight of 10000-30000D, the content of protein being greater than 6%.

17. The shampoo of claim 2, wherein the polyol is selected from glycerin, xylitol, sorbitol or a mixture thereof.

\* \* \* \* \*